US008008227B2

(12) United States Patent
Fischer et al.

(10) Patent No.: US 8,008,227 B2
(45) Date of Patent: Aug. 30, 2011

(54) MIXED OXIDE CATALYSTS FOR THE CATALYTIC GAS-PHASE OXIDATION OF OLEFINS AND PROCESSES FOR PRODUCING THEM

(75) Inventors: Achim Fischer, Aschaffenburg (DE); Werner Burkhardt, Brachttal (DE); Christoph Weckbecker, Gründau-Lieblos (DE); Klaus Huthmacher, Gelnhausen (DE); Frank Wilz, Alzenau (DE)

(73) Assignee: Evonik Degussa GmbH, Essen (DE)

( * ) Notice: Subject to any disclaimer, the term of this patent is extended or adjusted under 35 U.S.C. 154(b) by 388 days.

(21) Appl. No.: 12/091,116

(22) PCT Filed: Sep. 15, 2006

(86) PCT No.: PCT/EP2006/066411
§ 371 (c)(1),
(2), (4) Date: Sep. 17, 2008

(87) PCT Pub. No.: WO2007/042369
PCT Pub. Date: Apr. 19, 2007

(65) Prior Publication Data
US 2009/0030230 A1     Jan. 29, 2009

(30) Foreign Application Priority Data

Oct. 14, 2005  (DE) .......................... 10 2005 049 717
Apr. 4, 2006   (DE) .......................... 10 2006 015 710

(51) Int. Cl.
    *B01J 25/00*     (2006.01)
(52) U.S. Cl. ........ 502/322; 502/214; 502/306; 502/309; 502/311; 502/314; 568/420
(58) Field of Classification Search ....................... None
    See application file for complete search history.

(56) References Cited

U.S. PATENT DOCUMENTS 4,267,386 A * 5/1981 Vanderspurt ................. 568/480

FOREIGN PATENT DOCUMENTS

| DE | 103 53 954 A1 | 6/2005 |
| EP | 0 460 932 A2 | 12/1991 |
| EP | 1 748 041 | 5/2009 |
| JP | 6-38918 | 5/1994 |
| WO | 01/83106 A2 | 11/2001 |
| WO | 2005/110960 | 11/2005 |

* cited by examiner

*Primary Examiner* — Sudhakar Katakam
(74) *Attorney, Agent, or Firm* — Smith, Gambrell & Russell, LLP

(57) ABSTRACT

The invention relates to mixed oxide catalysts for the catalytic gas-phase oxidation of olefins and methylated aromatics, processes for producing the catalysts and the reaction with air or oxygen in the presence of inert gases in various ratios at elevated temperatures and pressure to form aldehydes and carboxylic acids.

30 Claims, No Drawings

MIXED OXIDE CATALYSTS FOR THE CATALYTIC GAS-PHASE OXIDATION OF OLEFINS AND PROCESSES FOR PRODUCING THEM

INTRODUCTION AND BACKGROUND

The invention relates to mixed oxide catalysts for the catalytic gas phase oxidation of olefins or methylated aromatics, to processes for preparing the catalysts and to the conversion to aldehydes and carboxylic acids with air or oxygen in the presence of inert gases in different quantitative ratios, at elevated temperatures and pressures.

In particular, the catalyst may be used to implement the highly exothermic reaction of propene to give acrolein and acrylic acid, or isobutene to give methacrolein and methacrylic acid. The highly exothermic reaction of the olefin over heterogeneous catalysts with an oxygen-containing gas leads, in addition to the desired acrolein and acrylic acid product, to a series of by-products, for example to the formation of $CO_2$, CO, acetaldehyde or acetic acid.

It is known that the type of chemical composition of the mixed oxide (phase formation and formation of reaction sites) and also the type of physical structure (for example porosity, surface size, shape of the catalyst), the type of heat removal, can greatly influence the ability to form product (selectivity) and the productivity (space-time yield). In the case of the olefin oxidation, the catalyst used is generally mixed oxides which have a complex chemical and physical structure. A multitude of publications describes mixed oxides which are capable of being used as catalysts for the preparation of acrolein and acrylic acid from propene. These catalysts consist generally of molybdenum, vanadium and/or tungsten. Generally at least one of the elements bismuth, antimony, vanadium, tellurium, tin, iron, cobalt, nickel and/or copper is added to these base components.

The number of publications on the heterogeneously catalysed gas phase oxidation of olefins to acrolein and acrylic acid is numerous since the first development GB 821999 (1958) for Standard Oil Inc. In spite of the long development time, it is still a demanding task to improve the performance of the catalyst, such as product yield, activity and lifetime. On this subject, the literature claims various techniques for preparation, and also formulations of the catalyst. By way of example, the most recent developments are explained here:

US 2005159621 describes a catalyst consisting of the base elements Mo, Bi, Fe, Cs. In addition, it is shown, as in the examples by the conversion of isobutene to methacrolein or propene to acrolein, that the highly toxic antimony is also required for this catalyst.

For the preparation of the catalyst, WO 2005/035115 utilizes the following manufacturing steps: preparation of a suspension which comprises the metal components, drying of the suspension, comminution of the dried material, mixing of the material with a sublimable substance, especially urea for pore generation, which is removed in the calcination. However, the removal of organic additives in the calcination harbours the risk of explosion; controlled removal of the organics is often impossible even with inert gas dilution. It is therefore doubtful whether such a process can be implemented on the production scale.

DE 103 53 954 utilizes catalysts of the $Mo_{12}W_bCo_cFe_dBi_eSi_fKgO_x$ type as annular unsupported catalysts in which the task of reducing the maximum temperature increase at high propene loading and hence of increasing the product selectivity is claimed. In the case of single throughput, the propene conversion is said to be greater than or equal to 90 mol % and hence the associated acrolein formation greater than or equal to 80 mol %. In the examples, yields of not more than 83.8% are shown.

WO 2005/063673 describes, for example, a method for diluting the catalyst with an inert material, in order to reduce the heat formation in the reaction zone and hence increase the product yield, by virtue of the avoidance of too high a hot spot reducing the total oxidation of the products. In spite of the temperature modulation of the reaction by inerts, the process described achieves only a total yield of acrolein and acrylic acid of not more than 91.22%. However, it would be more advisable to improve the yield of the catalyst directly. This would allow time-consuming and cost-intensive multizone filling of the reactor to be avoided.

SUMMARY OF THE INVENTION

It is generally accepted that highly specific local electronic structures of the catalytically active material are essential for the catalytic performance. These structures are laid down at an early stage, by the manufacturing steps of the catalyst precursors and the way in which these manufacturing steps are performed. For instance, a small change in one production parameter (concentration, temperature, etc.) can already lead to the catalyst being more active and more selective or less active and less selective.

It is an object of the present invention to improve the catalytic activity and selectivity of the catalyst compared to the prior art.

It is a further object of the invention to provide an improved process for preparing aldehydes and acids, in which acrolein and acrylic acid are prepared from propene by oxidation with air or oxygen in the presence of inert gases, including steam or offgases from the reaction, at elevated temperatures and in the presence of a heterogeneous mixed oxide catalyst. A mixed oxide catalyst shall be provided with which not only propene conversions greater than 95% but also a high product selectivity of greater than or equal to 88% is achieved, so that the economic viability of the process improves.

The olefin is converted to the aldehyde and acid oxidation product at relatively high temperatures and a ratio between olefin, air and inert gas(es) of preferably 1:6-9:3-18.

The inert gases used can be all gaseous compounds which behave inertly under the oxidation conditions described. For example, these may be nitrogen, helium, ethane, propane, steam or mixtures thereof. It is likewise possible to feed the "cycle gas" from the reactor back in. The steam may stem from the reaction or be added.

The invention provides mixed oxide catalysts of the general formula $$(Mo_{12}Bi_aC_b(Co+Ni)_cD_dE_eF_fG_gH_h)O_x \qquad (1)$$

in which:

C: iron,
D: at least one of the elements from W, P,
E: at least one of the elements from Li, K, Na, Rb, Cs, Mg, Ca, Ba, Sr,
F: at least one of the elements from Ce, Mn, Cr, V
G: at least one of the elements from Nb, Se, Te, Sm, Gd, La, Y, Pd, Pt, Ru, Ag, Au,
H: at least one of the elements from Si, Al, Ti, Zr
and
a=0-5.0
b=0.5-5.0
c=2-15
d=0.01-5.0
e=0.001-2
f=0.001-5
g=0-1.5
h=0-800,
x number which is determined by the valency and frequency of the elements other than oxygen.

The use of the inventive catalysts leads to a distinctly improved product selectivity of greater than or equal to ($\geqq$) 88% at high propene conversions of greater than or equal to ($\geqq$) 95%.

The novel process for preparing the catalysts with the general formula I allows a particularly suitable catalytically active solid to be obtained, for example, for the conversion of propene to acrolein and acrylic acid. The reaction is carried out particularly advantageously in reactors which allow the catalyst to be used as a fixed bed. However, it is likewise possible to apply the catalyst to the wall of the reaction chamber. At this point, it should be noted that catalysts of the general formula I can also be utilized to convert isobutene to methacrolein and methacrylic acid. It is likewise possible to convert toluene to benzaldehyde and benzoic acid.

The inventive catalysts can be prepared by obtaining a finely divided powder by the manufacturing steps of: dissolving the metal salts, precipitating the active components, drying and calcination. It is advisable to grind the dried or calcined powder. The calcined powder can be shaped. This can be done by tabletting, extrusion or by coating a support. The support type or support shape is not limiting. For example, the support may, for example, be a pyramid, a cylinder or a sphere. However, it may also constitute a wall of the reactor. Particular preference is given to the extrusion and coating of a round support. The catalyst can thus be used as a fixed bed catalyst. The support material may be a metal alloy, a common steel, a high-temperature polymer, a ceramic or ceramic raw materials. Should a shaping be required, it is then appropriate to interrupt the calcination in the temperature range from 420 to 490° C., then to perform the shaping, in order then to continue the calcination within the temperature range from 490 to 600° C. The catalyst thus prepared has an excellent activity, selectivity and lifetime, and leads to a very good product yield.

DETAILED DESCRIPTION OF THE INVENTION

The catalysts to be used for gas phase oxidation in the process described are obtained by combining the dissolved compounds with the desired concentrations of the catalytically active elements from the formula I. The components are ideally used in the form of the compounds selected from the group of ammonium or amine compounds, oxalates, carbonates, phosphates, acetates, carbonyls and/or nitrates, individually or together. Particular preference is given to carbonates, nitrates and phosphates or mixtures thereof. It is likewise possible to use acids of the salts, for example nitric acid, phosphoric acid or carbonic acid.

As already mentioned, the first stage of the catalyst preparation is a precipitation. It has been found that, in a preferred embodiment, the concentration of the metal counterions during the precipitation and their molar ratios have high significance for the catalytic performance of the oxidation catalyst.

Particularly active and selective catalysts of the general formula I are obtained when the molar ratios of the counterions are represented by $$R1=[NH_4^+]/[NO_3^-]=1/10–1/1 \text{ and/or}$$

$$R2=[NO_3^-]/([NO_3^-]+[CO_3^{2-}]+PO_4^{3-}+[Y-COO^-])=0.5–1/1$$

and Y may be any radical, especially methyl or ethyl, and the concentration of one or more of the ions, apart from $NO_3^-$ and $NH_4^+$, may also be zero.

Depending on the type of the metal salts which are used in the precipitation, it may be necessary to add salts, acids or solutions thereof to the precipitation mixture, in order to establish the preferred ion ratio R1 and/or R2. Ideally, use is made here of ammonia or ammonium salts, for example ammonium carbonate, ammonium heptamolybdate or metal nitrates, for example iron nitrate, cobalt nitrate; it is likewise possible to use the corresponding acids, for example nitric acid, in the amounts needed to establish the ionic ratio. The pH value during the precipitation is <8, in particular <7.

Likewise of significance is the temperature of the precipitation solution. It may be that the activity of the catalyst is distinctly reduced at excessively high temperature. The precipitation can in principle be carried out at temperatures of 5 to 90° C. However, it has been found that a catalyst whose precursor has been precipitated at temperatures of 20 to 50° C. is distinctly more active.

The preparation of the coprecipitate can be performed in one precipitation stage. It is more preferable to perform the precipitation in several stages by stepwise addition of the individual components or else mixtures thereof. The number of precipitation stages is in principle not limited. However, preference is given to one to three precipitation stages.

The resulting suspension can be processed further directly or it is matured for >0 to 24 hours, preferably >0 to 12 hours, more preferably 0 to 6 hours. It is self-evident that the precipitation suspension is homogenized before the further processing, for example by stirring.

After the maturing, the liquid of the suspension can be removed by evaporation, centrifugation or filtration. It is likewise possible to evaporate the liquid and simultaneously to dry the solid, which can be effected, for example, by spray-drying. The liquid should be evaporated at a temperature of 80 to 130° C. The drying of the solid can be effected with air, oxygenous inert gases or inert gases, for example nitrogen. When the drying is carried out in an oven, the temperature should be between 100 and 200° C. In a spray dryer, the starting temperature of the drying medium should be 200 to 500° C. and provide for a temperature on deposition of the dried powder of 80 to 200° C. The resulting particles should preferably have a particle size distribution of 15 to 160 µm with a mean particle diameter between 15 and 80 µm.

The dried powder can in principle be calcined in a wide variety of different oven types, for example in a forced-air oven, rotary tube, tray oven, shaft oven or belt oven. The control quality and the quality of temperature detection in the oven should be as high as possible. The residence time of the powder in the oven should, depending on the oven type, be between 0.25 and 13 h.

It is likewise possible to perform the calcination and the thermal decomposition of the salts which occurs in the course thereof in one or more stages. Temperatures of 200 to 600° C., in particular 300 to 600° C., may be utilized. The thermal decomposition can be performed with addition of inert gas, composed of mixtures of oxygen with an inert gas.

Examples of usable inert gases are nitrogen, helium, steam or mixtures of these gases.

It has been found that comminution of the powder after the spray-drying or the calcination is advantageous for the activity. The comminution can be achieved in dry form or as an aqueous suspension, for example by grinding. However, it is advantageous to perform the comminution after the calcination or, in the case of a multistage calcination, between individual calcination stages. The powder thus obtained can be used as a catalyst. The mean particle size distribution of the powder should range from 0.01 to 50 µm. Particular preference is given to a mean particle size distribution of 0.1 to 30 µm. For industrial use, it is particularly appropriate, after addition of commercial shaping agents and binders, to shape the powder. This can be done by tabletting, extrusion or by coating of a support. The geometric shape of the support here is not limiting. Instead, it is guided by the prerequisites of the reactor (for example tube diameter, length of the catalyst bed). For example, the support may be a pyramid, a cylinder, a saddle, a sphere or a polygon, but it may also be a wall of a reaction chamber.

The binders used may be various oils, celluloses, polyvinyl alcohols, saccharides, acrylates and alkyl derivatives, mixtures or condensates thereof. Preference is given to acrylates, polyvinyl alcohols and celluloses. Particular preference is given to derivatives and condensates of acrylates and/or celluloses, and also mixtures thereof.

In the case of shaping of the catalyst powder, the catalyst should preferably be aftertreated thermally within the temperature range from 490 to 600° C., so that the active composition for use in industrial reactors solidifies.

The invention likewise provides for the oxidation of olefins to unsaturated aldehydes and corresponding acids in the presence of the inventive catalysts.

The reaction to prepare acrolein and acrylic acid is carried out generally at temperatures of 250-450° C. and a pressure of 1.0-2.2 bara. The olefin, air and inert gas reactants are preferably fed to the catalyst bed in a ratio of 1:6-9:3-18 at a loading of 2-10 mol of olefin/dm$^3$ of catalyst bed/h.

Propene is used to prepare acrolein and acrylic acid in particular as chemical-grade or polymer-grade propene, but it is also possible to utilize refinery-grade propene. Instead of inert gas, the offgas from the reaction can be used, from which the condensable constituents have been removed. Particularly good results are obtained in the case of use of tube bundle reactors, plate reactors (for example EP 0 995 491; EP 1 147 807) or wall reactors (for example Redlingshoefer H., Fischer A., et al., Ind. Eng. Chem. Res. 2003, 42, 5482-5488; EP 1 234 612) in which the catalyst is applied to the wall.

The internal diameter of the reaction tubes or the separation of the plates should be 18 to 28 mm, preferably 20 to 26 mm; the wall thickness of the iron-containing steel should be between 1 and 3.5 mm. A typical reactor length is 3.00 to 4.00 m. The catalyst is preferably used uniformly along the reactor length without dilution with shaped diluent bodies; of course, the application may necessitate, for example, dilution with inert shaped bodies.

Even in the case of high specific loading, the inventive catalysts lead to an improved activity and selectivity in the case of use in the oxidation processes mentioned.

The invention is illustrated below with reference to working examples. In the examples, the yield (%) of the product is defined as (mol/h of product formed)/(mol/h of reactant supplied)×100, the conversion of the olefin (%) is defined as

[1−(mol/h of olefin leaving the reaction tube)/(mol/h of olefin entering the reaction tube)]×100, the selectivity (%) is defined as (yield of the product/conversion)×100

In order to improve understanding, the invention illustrated is described by the examples which follow, but is not restricted to these examples.

EXAMPLES

Example 1

A solution I was prepared by dissolving the nitrates of iron, cobalt, nickel, manganese, potassium in the proportions by mass 23.2:47.26:29.28:0.0646:0.2067 in 3.5 litres of water, and heated to 40° C. with stirring, and a nitric acid solution of 0.1 mol of Sm$^{3+}$ and 2 mol of HNO$_3$ was added.

For a solution II, a solution of 2118.6 g of ammonium heptamolybdate in 2.7 l of water was prepared at 40° C., 4.4 g of phosphoric acid and 0.42 g of Aerosil 200 (Degussa), 14 g of aluminium oxide in 1 l of water were added thereto.

Solution II was added to solution I slowly and with vigorous stirring. In a separate vessel, a further solution III consisting of 790 g of bismuth nitrate and 0.72 mol of HNO$_3$ was made up. Addition of this solution to the other active components afforded the coprecipitate for the preparation of the active catalyst phase.

The coprecipitate was stirred intensively for 12 hours. The resulting suspension was dried in a spray dryer with rotating disc at a gas entrance temperature of 350° C. The air rate was adjusted so as to obtain an exit temperature of 110+/−10° C.

The resulting mean particle diameter of the powder thus prepared was 55 µm. This powder was treated in a forced-air oven at a temperature of 445° C. for 1 hour until a mixed oxide formed, which was ground in the next step to a mean particle diameter of 1 µm. The mixed oxide was sprayed as an aqueous suspension through a two-substance nozzle onto a ceramic spherical catalyst support and dried at 60° C. in an air stream. To homogenize the pellets, they were circulated in a drum. To solidify the active composition applied, the material obtained was heated to 540° C. for 1 hour.

The catalyst thus prepared had the composition:
$(Mo_{12}Bi_{1.5}(Co+Ni)_{8.0}Fe_{1.8}Mn_{0.01}$
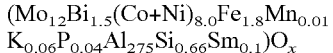

Example 2a

The catalyst of Example 1 was contacted with a mixture of composition of 7.5% by volume of propene (chemical-grade), 58% by volume of air and inert gas (100% by volume in total). The total gas flow rate was 36.9 l/min. The temperature of the heat carrier was 340° C. The conversion of the propene was 94 mol %; the product selectivity for acrolein and acrylic acid was 96%.

Example 2b

The prepared catalyst of Example 1 was contacted with a mixture of composition of 7.8% by volume of propene (chemical-grade), 12.1% by volume of oxygen, 3.9% by volume of water and nitrogen. The total gas flow rate was 27.5 l/min. The temperature of the heat carrier was 334° C. This formed undesired by-products with a selectivity of 4%.

Example 2c

The prepared catalyst of Example 1 was contacted with a mixture of composition of 4.6% by volume of propene (chemical-grade), 47% by volume of air and 47% by volume of inert gas. The total gas flow rate was 1100 l/h. The temperature of the heat carrier was selected such that the conversion of the propene was 93 mol %; the yield of acrolein was 88%.

Example 2d

The prepared catalyst of Example 1 was contacted with a mixture of composition of 5.8% by volume of propene (chemical-grade), 51% by volume of air, 46% by volume of inert gas. The total gas flow rate was 20 l/min. The temperature of the heat carrier was selected such that the conversion of propene was 92 mol %; the selectivity for acrolein was 92%.

Example 2e

The prepared catalyst of Example 1 was contacted with a mixture of composition of 6.2% by volume of propene (chemical-grade), 55% by volume of air and nitrogen. The total gas flow rate was 22.2 l/min. The temperature of the heat carrier was 327° C.; the propene conversion was 96 mol %; the selectivity for acrolein was 91%.

Example 3

The calcined mixed oxide was prepared as described in Example 1. 1.6 kg of the mixed oxide powder are mixed with 0.4 kg of pentaerythritol (ground ultrafine). A 6% methylcellulose solution was introduced into this mixture which was kneaded until a homogeneous, plastic mass was obtained, which was extruded under constant pressure as a pellet with a diameter of 3 mm and a length of 5 mm and dried at 10° C.

The extrudate was solidified in a rotary tube oven. To this end, the feed and rotational speed are adjusted to one another such that the residence time in the tube was 20 minutes. The peak temperature of the tube was 580° C.

Example 4

The catalyst of Example 3 was contacted with a mixture of composition of 7.3% by volume of propene (chemical-grade), 57% by volume of air and inert gas. At a bath temperature of 308° C. and a contact time of 2.9 s, acrolein and acrylic acid were obtained with a selectivity of 94% at a conversion of 90%.

Example 5

A solution I was prepared by dissolving the nitrates of iron, cobalt, nickel, manganese, potassium in the proportions by mass of 37.16:31.24:31.22:0.06133:0.3095 in 3.5 l of water, heating to 40° C. with stirring and adding a nitric acid solution composed of 0.1 mol of $Sm^{3+}$ and 2 mol of $HNO_3$. For a solution II, a solution of 2119 g of ammonium heptamolybdate in 2.7 l of water was prepared at 40° C.; 4.4 g of phosphoric acid and 0.4 g of Aerosil 200 (Degussa), 14 g of aluminium oxide in 1 l of water were added thereto.

Solution II was added slowly and with vigorous stirring to solution I. In a separate vessel, a further solution consisting of 776 g of bismuth nitrate and 0.72 mol of $HNO_3$ was made up. Addition of this solution to the other active components afforded the coprecipitate.

The coprecipitate was stirred intensively for 12 hours. The resulting suspension was dried in a spray dryer with rotating disc at a gas entrance temperature of 350° C. The air rate was adjusted such that an exit temperature of 110+/−10° C. was obtained.

The resulting mean particle diameter of the powder thus prepared was 55 µm. The powder thus obtained was treated in a forced-air oven at a temperature of 445° C. for 1 hour, so that the mixed oxide was formed.

The mixed oxide was sprayed as an aqueous suspension through a two-substance nozzle onto a ceramic spherical catalyst support and dried in a constant airstream. To homogenize the pellets, they were circulated in a drum.

To solidify the active composition applied, the material obtained was heated to 540° C. for 2 hours.

The catalyst thus prepared has the composition: $(Mo_{12}Bi_{1.6}Co_{3.4}Fe_{2.9}Ni_{3.4}Mn_{0.01}K_{0.1}P_{0.04}Al_{275}Si_{9.35}Sm_{0.1})O_x$

Example 6

The catalyst of Example 5 was contacted with a mixture of composition of 7.3% by volume of propene (chemical-grade), 57% by volume of air and inert gas. At a bath temperature of 350° C. and a contact time of 2.7 s, acrolein and acrylic acid were obtained with a selectivity of 96% at a conversion of 93%.

Example 7

A solution I was prepared by dissolving the nitrates of iron, cobalt, nickel, manganese, potassium in the proportions by mass of 23.2:47.26:29.28:0.0646:0.2067 in 3.5 litres of water and heating to 40° C. with stirring and adding a nitric acid solution composed of 0.1 mol of $Sm^{3+}$ and 2 mol of $HNO_3$.

For a solution II, a solution of 2118.6 g of ammonium heptamolybdate in 2.7 l of water was prepared at 40° C., 4.4 g of phosphoric acid were added thereto.

Solution II was added to solution I slowly and with vigorous stirring. In a separate vessel, a further solution III consisting of 790 g of bismuth nitrate and 0.72 mol of $HNO_3$ was made up. Addition of this solution to the other active components afforded the coprecipitate for the preparation of the active catalyst phase.

The coprecipitate was stirred vigorously for 12 hours. The resulting suspension was dried in a spray dryer with rotating disc at a gas entrance temperature of 350° C. The air rate was adjusted such that an exit temperature of 110+/−10° C. was obtained.

The resulting mean particle diameter of the powder thus prepared was 55 µm. The powder thus obtained was treated in a forced-air oven at a temperature of 445° C. for 1 hour, so that the mixed oxide was formed.

The mixed oxide was sprayed as an aqueous suspension whose solid has a mean particle diameter (D50 value) of 1 µm through a two-substance nozzle onto a ceramic spherical catalyst support and dried in a constant air stream. To homogenize the pellets, they were circulated in a drum. To solidify the active composition applied, the resulting material was heated to 540° C. for 2 hours.

The catalyst thus prepared has the composition: $(Mo_{12}Bi_{1.5}(Co+Ni)_{8.0}Fe_{1.7}Mn_{0.01}K_{0.06}P_{0.04}Sm_{0.1})O_x$

Example 8

The prepared catalyst of Example 5 was contacted with a mixture of composition of 7.3% by volume of propene (chemical-grade), 57% by volume of air and inert gas. At a bath temperature of 333° C. and a contact time of 2.5 s, acrolein was obtained with a selectivity of 89% at a conversion of 92%.

Example 9

The preparation method of Example 1 was changed such that the catalyst has the composition: $(Mo_{12}Bi_{1.6}(Co+Ni)_{8.12}Fe_{1.8}Mn_{0.008}K_{0.06}P_{0.004}Al_{275}Si_{0.65}Sm_{0.1})O_x$.

Example 10

The prepared catalyst of Example 9 was contacted with mixture of composition of 3% by volume of propene (chemical-grade), 43% by volume of air, 5.2% by volume of water and inert gas. The total gas flow rate was 16 l/min. The temperature of the heat carrier was selected such that the conversion of the propene was 97 mol %; the yield of acrolein was 87%.

Counterexample 1

The catalyst was prepared as described in Example 1 at a solution temperature of 80° C.

The catalyst thus prepared was contacted with a mixture of composition of 7.5% by volume of propene (chemical-grade), 58% by volume of air and inert gases. The maximum possible total gas flow rate was only 28.2 l/min. The temperature of the heat carrier was 15° C. higher than in Example 2a; in spite of this, a propene conversion of only 91% was obtained; the acrolein yield was only 82%. The catalyst is consequently significantly less active.

Counterexample 2

In order to be able to establish a propene conversion of 97% with the prepared catalyst from counterexample 1, it was necessary to reduce the total gas flow rate to 18.9 l/h and the volume fraction of propene to 4.5% by volume of propene (chemical-grade). The catalyst consequently had a distinctly lower activity.

Counterexample 3

The preparation of the catalyst is carried out as described in Example 1. However, solution II was initially charged, then solution III and finally solution II were added.

The catalyst thus prepared achieved a maximum selectivity of acrolein of 85% at a propene conversion of 96% (selectivity for acrolein and acrylic acid of 88%).

The catalyst thus prepared was consequently significantly less selective.

Counterexample 4

The preparation of the catalyst is carried out as described in Example 1, except that the mean particle diameter in the coating suspension is 25 μm.

The catalyst is tested under conditions of Example 2a. It was necessary to set a bath temperature 15° C. higher, but the resulting propene conversion was only 88 mol %. The catalyst was consequently significantly less active.

The invention claimed is:

1. A mixed oxide catalyst of the formula

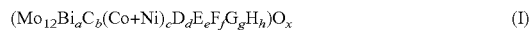

$$(Mo_{12}Bi_aC_b(Co+Ni)_cD_dE_eF_fG_gH_h)O_x \quad (I)$$

in which
  C: iron,
  D: at least one of the elements selected from the group consisting of W and P,
  E: at least one of the elements selected from the groups consisting of Li, K, Na, Rb, Cs, Mg, Ca, Ba and Sr,
  F: at least one of the elements selected from Ce, Mn, Cr and V G: at least one of the elements selected from the groups consisting of Nb, Se, Te, Sm, Gd, La, Y, Pd, Pt, Ru, Ag and Au
  H: at least one of the elements selected from the groups consisting of Si, Al, Ti and Zr
and
a=0-5.0
b=0.5-5.0
c=2-15
d=0.01-5.0
e=0.001-2
f=0.001-5
g=0-1.5
h=0-800,
and
x=number which is determined by the valency and frequency of the elements other than oxygen, and g+h>0.

2. A mixed catalyst according to claim 1, wherein the mixed oxides have been applied to support materials.

3. Process for preparing a mixed oxide catalyst of the formula I, according to claim 1 wherein solutions of compounds of the metals present in the mixed oxide catalysts of the formula I are mixed, coprecipitates are prepared, and the resulting solid is isolated, dry-calcined and optionally reshaped.

4. Process according to claim 3, wherein the pH during the precipitation of the solid(s) is <8.

5. Process according to claim 3, wherein metal compounds selected from the group consisting of ammonium or amine compounds, oxalates, carbonates, phosphates, acetates, carbonyls, nitrates and mixtures thereof are used individually or together.

6. Process according to claim 3, wherein carbonates, nitrates or phosphates, or mixtures of these salts are used.

7. Process according to claim 3, wherein acids corresponding to the anions of the salts used are optionally used.

8. Process according to claim 3, wherein the molar ratios of the metal counterions in the precipitation are represented by $$R1=[NH_4^+]/[NO_3^-]=1/10-1/1 \text{ and/or}$$

$$R2=[NO_3^-]/([NO_3^-]+[CO_3^{2-}]+[PO_4^{3-}]+[Y\text{-}COO^-])=0.5-1/1$$

where Y
  is $CH_3$ or $C_2H_5$, and $[NO_3^-]$ and $[NH_4^+]$ are each >0.

9. Process according to claim 3, wherein ammonia or ammonium salts, or metal nitrates, and/or the corresponding acids, are used to prepare the coprecipitate.

10. Process according to claim 3, wherein the precipitation is carried out at temperatures of 5 to 90° C.

11. Process according to claim 10, wherein the precipitation is carried out at temperatures of 20 to 50° C.

12. Process according to claim 3, wherein the suspension obtained by precipitation matures for 0 to 24 hours.

13. Process according to claim 3, wherein the dried powder, before the calcination, consists of spray-dried particles having a particle size distribution of 15 to 160 μm.

14. Process according to claim 13, wherein the mean particle size distribution of the dried coprecipitate is between 15 μm and 80 μm.

15. Process according to claim 3, wherein the residence time of the dried powder in the oven for calcination is between 0.25 and 13 h, in the course of which temperatures of 200 to 600° C. are established.

16. Process according to claim 3, wherein the calcination is carried out in one or more stages.

17. Process according to claim 15, wherein the calcination is carried out with addition of inert gas, from mixtures of oxygen with an inert gas in the presence or absence of steam.

18. Process according to claim 15, wherein the calcined powder is fixed by tabletting, extrusion or coating of a support.

19. Process according to claim 15, wherein the particle size distribution of the calcined or partly calcined powder, is between 0.01 and 80 µm.

20. Process according to claim 3, wherein the particle size distribution of the spray-dried powder, if appropriate by virtue of grinding, is between 0.1 and 50 µm.

21. Process according to claim 3, wherein the mean particle size distribution of the calcined or partly calcined powder, can be adjusted to a distribution of 0.01 to 30 µm.

22. Process according to claim 3, wherein shaping of the catalyst powder is followed by a thermal treatment in the temperature range of 450 to 600° C.

23. Process for preparing aldehydes and acids by oxidizing olefins or methylated aromatics with air or oxygen in the presence of inert gases, steam or offgases from the reaction at elevated temperatures, characterized in that a catalyst of the general formula

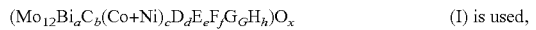
$$(Mo_{12}Bi_aC_b(Co+Ni)_cD_dE_eF_fG_gH_h)O_x \quad (I) \text{ is used,}$$

in which
C: iron,
D: at least one of the elements selected from the groups consisting of W and P,
E: at least one of the elements selected from the groups consisting of Li, K, Na, Rb, Cs, Mg, Ca, Ba and Sr,
F: at least one of the elements selected from the groups consisting of Ce, Mn, Cr and V
G: at least one of the elements selected from the groups consisting of Nb, Se, Te, Sm, Gd, La, Y, Pd, Pt, Ru, Ag and Au
H: at least one of the elements selected from the groups consisting of Si, Al, Ti and Zr
and
$a=0-5.0$
$b=0.5-5.0$
$c=2-15$
$d=0.01-5.0$
$e=0.001-2$
$f=0.001-5$
$g=0-1.5$
$h=0-800$,
and
x=number which is determined by the valency and frequency of the elements other than oxygen, and $g+h>0$.

24. Process according to claim 23, wherein acrolein and acrylic acid are obtained from propene.

25. Process according to claim 23, wherein methacrolein and methacrylic acid are obtained from isobutene.

26. Process according to claim 23, wherein benzaldehyde and benzoic acid are obtained from toluene.

27. Process according to claim 23, wherein the catalyst is contacted with a reaction gas mixture which comprises olefin or methylated aromatics, air, inert gases in a ratio of 1:6-9:3-18.

28. Process according to claim 3 wherein ammonium carbonate, ammonium heptamolybdate, iron nitrate or cobalt nitrate are used to prepare the coprecipitate.

29. Process according to claim 3 wherein the suspension obtained by precipitation matures for ≧0 to 12 hours.

30. Process according to claim 3 wherein the suspension obtained by precipitation matures for ≧0 to 6 hours.

* * * * *